Figure 1:
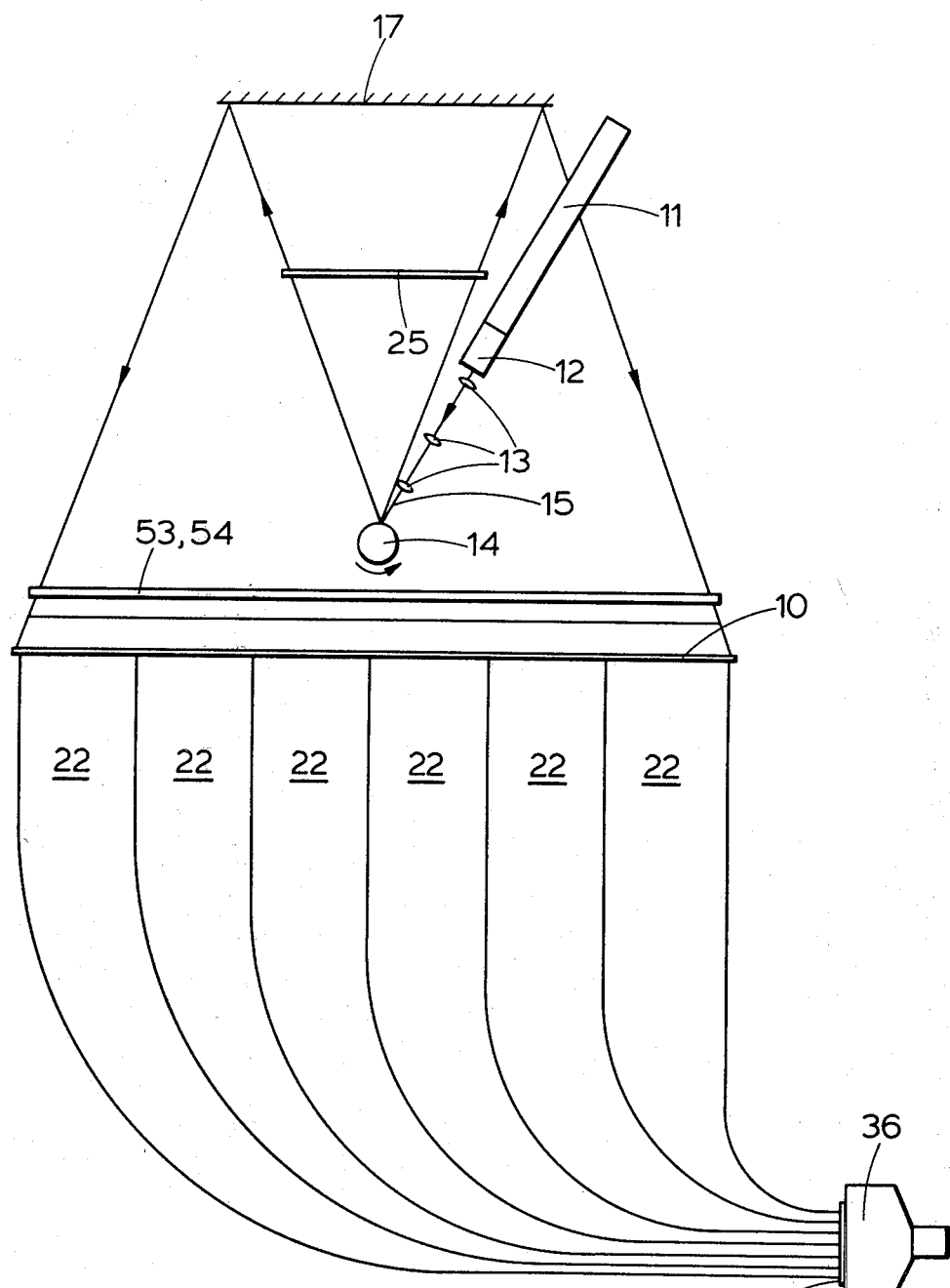

United States Patent [19]

West et al.

[11] 4,323,311
[45] Apr. 6, 1982

[54] APPARATUS AND METHOD FOR DETECTING HOLES IN SHEET MATERIAL

[75] Inventors: Robert N. West; Patricia A. West, both of Chislehurst; Andrew J. Barker, Orpington; Rosemary J. Hall, Havant, all of England

[73] Assignee: Sira Institute Limited, Chislehurst, England

[21] Appl. No.: 144,938

[22] Filed: Apr. 29, 1980

[30] Foreign Application Priority Data

May 11, 1979 [GB] United Kingdom ............... 16525/79

[51] Int. Cl.$^3$ ........................................... G01N 21/89
[52] U.S. Cl. .................................... 356/431; 250/572
[58] Field of Search ................ 356/431; 250/563, 572

[56] References Cited

U.S. PATENT DOCUMENTS 4,011,457 3/1977 Wolf .................................... 356/431
4,118,127 10/1978 Klein et al. ......................... 250/572
4,173,441 11/1979 Wolf .................................... 250/563

Primary Examiner—R. A. Rosenberger
Attorney, Agent, or Firm—Hane, Roberts, Spiecens & Cohen

[57] ABSTRACT

Method and apparatus for detecting holes in sheet material such as tin plate where a beam from a laser is scanned across the sheet by a mirror drum, successive scans being arranged to strike the sheet material from upstream and downstream, and the light passing through a hole in the sheet material is received by a perspex light guide and passed to a photodetector.

31 Claims, 10 Drawing Figures

APPARATUS AND METHOD FOR DETECTING HOLES IN SHEET MATERIAL

The present invention relates to apparatus and a method for detecting holes in sheet material.

Sheet material is generally manufactured in a continuous process and a strip of the sheet material is transported through a series of rolls, and in many processes is then cut into strips and stacked. Clearly it is desirable to inspect the sheet material after it has been rolled and before it is cut and stacked.

The apparatus and method to be described as preferred embodiments of the invention relate to methods of inspecting tin plate but is applicable to other sheet material such as paper.

The present invention provides apparatus for detecting holes through opaque or generally opaque sheet material moving in a first direction comprising a radiation source, means for directing a beam of radiation from the source at the sheet material and for scanning the beam thereacross in a direction transverse to said first direction, characterised in that said beam directing means is arranged so that the beam, in use, is directed at said sheet material along a path tilted from the perpendicular to the sheet material in an upstream direction with respect to the direction of movement of the sheet material during some scans and in a downstream direction during other scans, means located so as to be on the opposite side of the sheet material to the incident radiation to collect radiation passing through holes in the sheet material, said collection means comprising at least one radiation guide comprising transparent material having a high refractive index relative to its surroundings, a first face of the radiation guide being shaped and positioned to collect the radiation passing through holes in the sheet material, a second face of the radiation guide opposite the first face being shaped to pass the radiation collected by the first face to a radiation detector, and the faces joining the first and second faces being arranged such as to internally reflect radiation from said first face to said second face.

The advantage of such arrangements is that where the holes are small and are at an angle to the surface of the sheet material (which frequently happens when the sheet material has been rolled), and it is generally found that such an angle is upstream or downstream with respect to the movement of the sheet, then such small holes are more readily detected.

Although the radiation to be used in the preferred embodiment is of optical wavelengths it will be understood that under many circumstances radiation of other wavelengths such as ultra-violet or infra-red may be used as applicable.

Although the broad aspect of the invention is not restricted thereto, it is preferable that the apparatus be arranged so as to be able to detect pin holes in the sheet material. Becuase pin holes tend to scatter radiation passing therethrough, conventional apparatus for collecting scanned radiation passing through the sheet would not be suitable.

In a preferred arrangement, the first face of the radiation guide is planar and rectangular, one pair of sides of the rectangle being parallel to the direction of scanning. Said one pair of sides is preferably longer than the other pair of sides.

The second face is preferably planar and generally rectangular, the radiation guide being of rectangular section between the first and second faces, each of the pair of sides of the rectangular section of the second face which corresponds to said one pair of sides being smaller than each of said one pair of sides.

There may be provided a plurality of radiation guides, each having generally similar shaped rectangular first faces, the radiation guides being arranged end to end so that their said one pair of sides are colinear and their first faces are coplanar. In this way, the light collection area provided is elongate and matches the line of scan. The second faces of said radiation guides are each generally similar and the second faces are coplanar and arranged side by side. In this manner the second faces may be readily matched to a single conventional photomultiplier.

The radiation guide is preferably of a material such as perspex having a refractive index with respect to air of approximately 1.5. Means may be provided to reduce the ambient light falling on the radiation collector.

Preferably the radiation source comprises a laser and the scanning means comprises a multi-faceted mirror drum.

Where the apparatus is for use with sheet material which reflects at least a proportion of the radiation incident on it, we may also preferably provide means for collecting radiation reflected by the sheet material to examine the surface of the sheet material for surface defects. The advantage of this is that we may thereby check the sheet material both for holes therethrough and for defects on its surface.

In this case, retro-reflection means may be provided to reflect back to the sheet material radiation which has been reflected by the sheet material. Means may then be provided for preventing radiation reflected by the retro-reflector and passing past the edge of the sheet material as the beam passes beyond the edge of the sheet material from reaching the radiation detector. In this case, the prevention means may comprise means for polarising the beam of radiation directed at the sheet material, means for rotating the plane of polarisation of the radiation reflected from the surface of the sheet material by 45° means for rotating the plane of polarisation of radiation reflected by the retro-reflector by 45°, and polarised filter means provided in front of the radiation collecting means, whereby radiation reflected by the sheet material, and the retro-reflecting material will not pass through the polarising filter.

The radiation detector preferably includes means for preventing the overloading of the radiation detector as the beam is scanned beyond the edge of the sheet material. This overload prevention means may either comprise an acousto-optical device in the beam path and signal processing means for detecting an excess signal produced by the radiation detector connected to switch the acousto-optical device to attenuate the beam or may comprise control means for detecting an excess signal in the radiation detector and reducing the sensitivity of the radiation detector means.

The radiation detector may be connected to pass a signal to a signal processing apparatus which includes a band pass filter arranged to pass a signal corresponding to a hole in the sheet material. In this way the signal to noise ratio is much improved.

The invention also provides, according to a further aspect, a method for detecting holes through an opaque or generally opaque sheet material moving in a first direction comprising directing a beam of radiation at the sheet material and scanning the beam thereacross, characterised by directing the beam at said sheet material along a path tilted from the perpendicular to the sheet material in an upstream direction with respect to the direction of movement of the sheet material during some scans and in a downstream direction during other scans, collecting radiation passing through holes in the sheet material by means of a radiation guide, the guide internally reflecting radiation received by a first face thereof so as to pass the radiation to a second face thereof, detecting radiation received at the second face and producing an output signal in accordance with the radiation detected.

Preferably the radiation is collected from an elongate area parallel with the line of scan, and is passed to a compact area adjacent the radiation detector whereby a single radiation detector is utilised.

The beam of radiation is preferably scanned across the sheet material in such a manner as to cover all the sheet material. The sheet material may be moved in a first direction preferably at a rate of 600 m/min and the beam is scanned in a direction transverse thereto.

If the sheet material to be inspected reflects at least a proportion of the radiation incident on it the method may include a further step of collecting radiation reflected by the surface of the sheet material to examine the surface of the sheet material for surface defects. In this case, the beam reflected from the sheet material is preferably retro-reflected back to the sheet material so as to be reflected a second time by the sheet material before collection. Then the radiation which has been retro-reflected has passed beyond the edge of the sheet material as the beam passes beyond the edge of the sheet material is preferably prevented from reaching the radiator detector. And this is preferably carried out by arranging that the incident beam is polarised, the plane of polarisation of the beam reflected by the material is rotated by 45° before reaching the retro-reflector, and the retro-reflected beam is polarised by a further 45°, and a polarised filter means situated before the radiation guide means is aligned so as to absorb the retro-reflected beam.

Overloading of the radiation detector may be prevented as the beam is scanned beyond the edge of the sheet material either by detecting an increase in the signal produced by the radiation detector and attenuating the incident beam in accordance therewith or by reducing the sensitivity of the radiation detector.

The method may be arranged so as to detect holes down to a size 100 $\mu m \times 100$ $\mu m$ and preferably at least down to a size 25 $\mu m \times 25$ $\mu m$.

Figure 2:
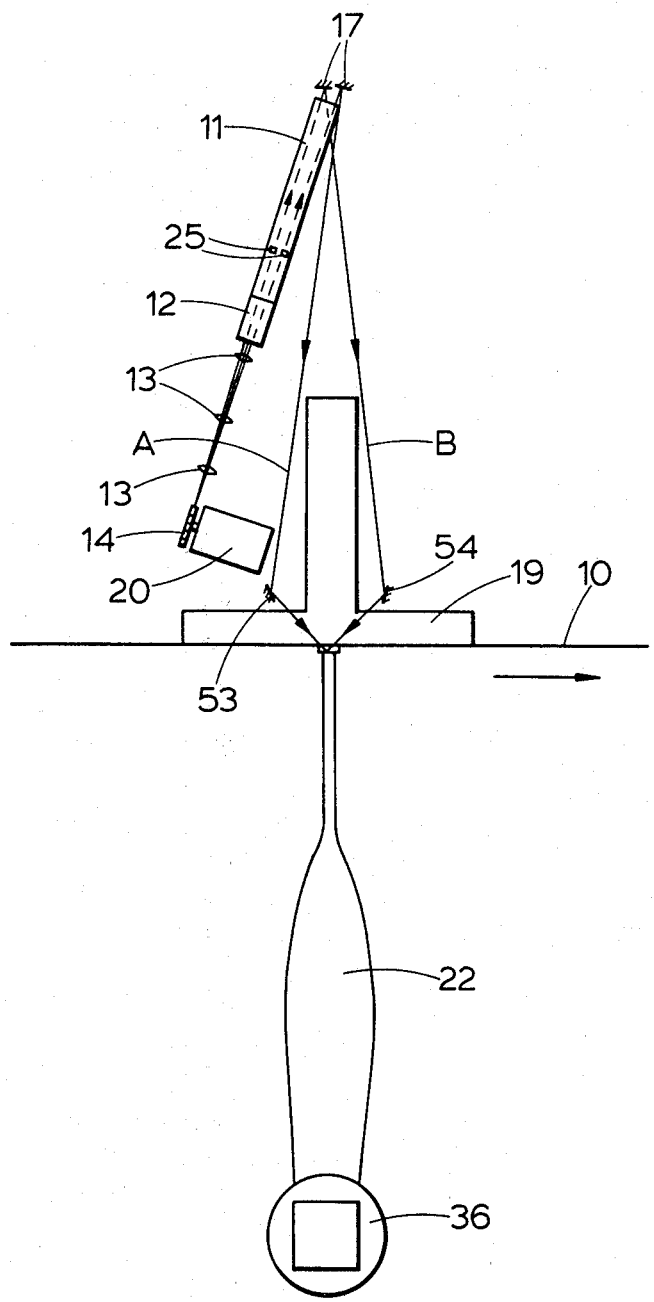
Figure 3:
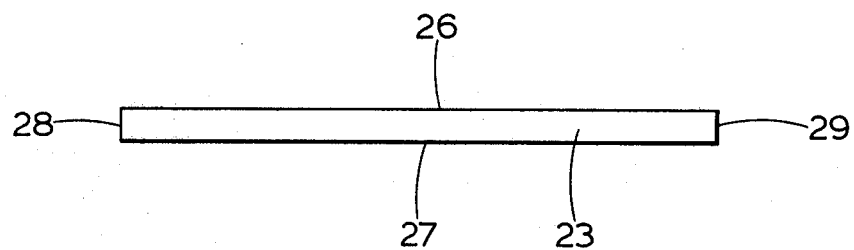
Figure 4:
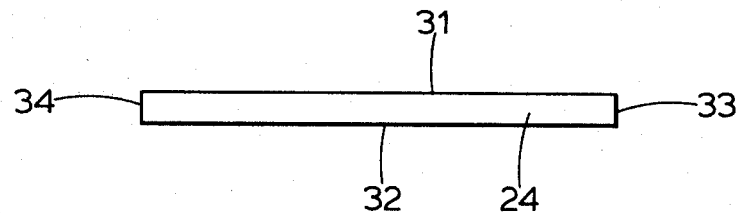
Figure 5:
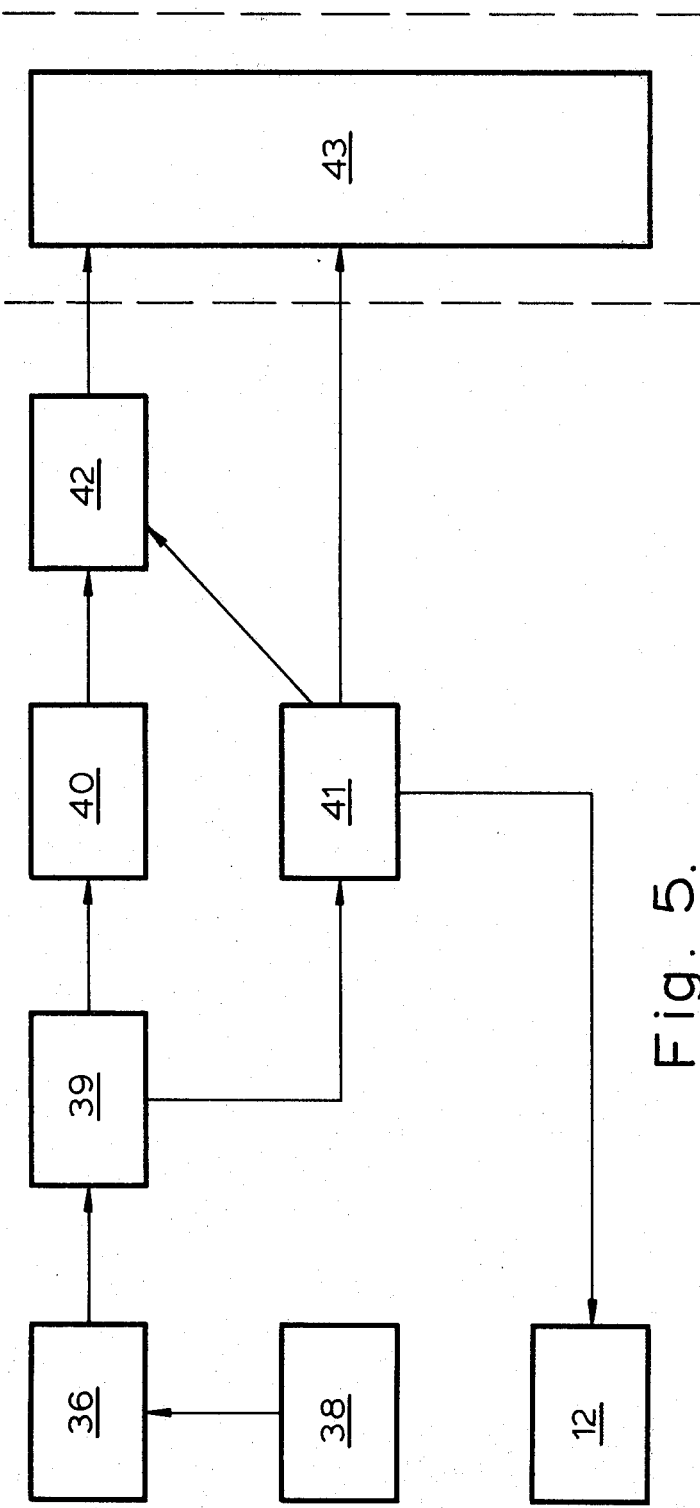
Figure 6:
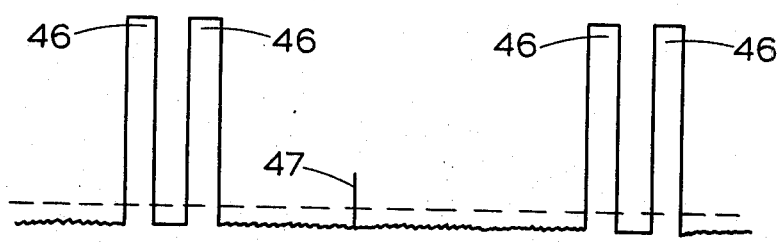
Figure 7:
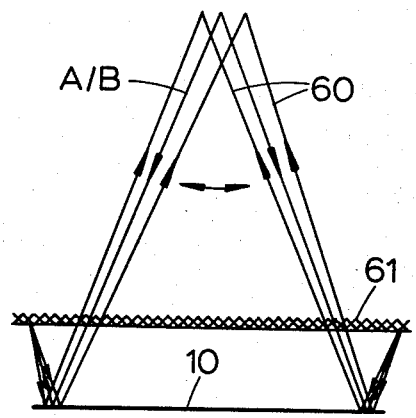
Figure 8:
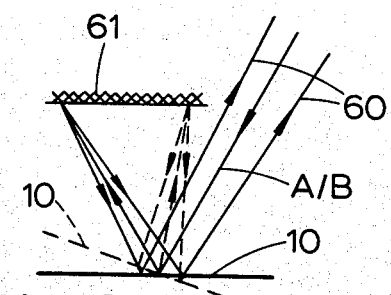
Figure 10:
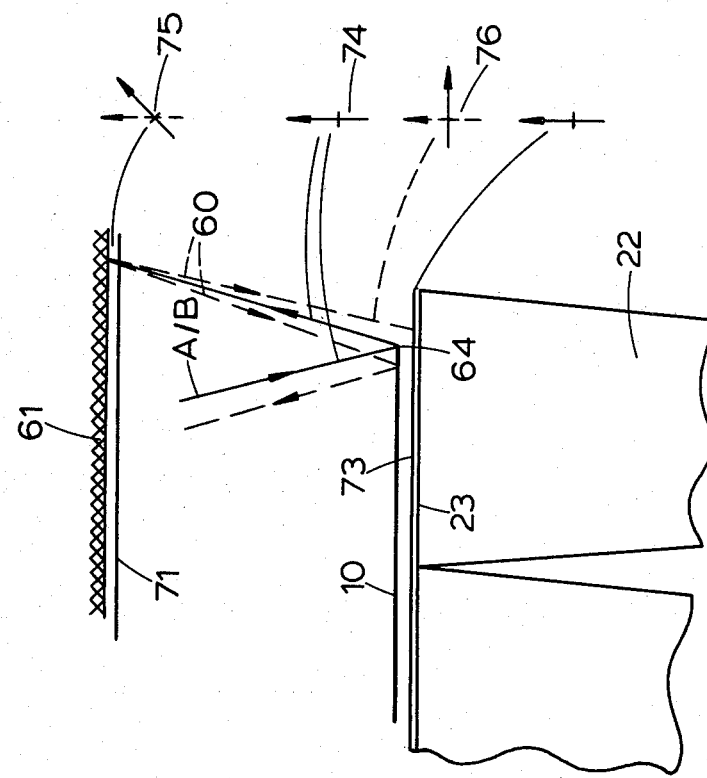
Figure 9:
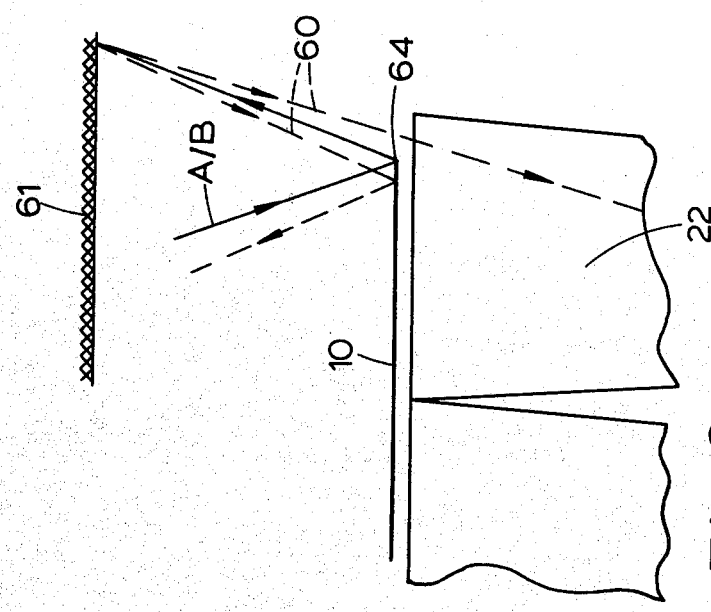

A preferred arrangement of apparatus for detecting holes will now be described by way of example only and with reference to the accompanying drawings in which:

FIG. 1 is an end view partly in section of the apparatus according to the invention, FIG. 2 is a side view of the apparatus of FIG. 1, FIG. 3 is a plan view of a first end face of a light guide of the apparatus of FIGS. 1 and 2, FIG. 4 is a plan view of a second end face of a light guide of the apparatus of FIGS. 1 and 2, FIG. 5 is a block circuit diagram of signal processing apparatus for processing the signal produced by the apparatus of FIGS. 1 and 2, FIG. 6 is a plot of the signal produced by the apparatus of FIGS. 1 and 2, FIG. 7 and FIG. 8 are end and side views respectively on an enlarged scale of part of the apparatus of FIGS. 1 and 2, FIG. 9 is a view of part of the apparatus of FIGS. 7 and 8, FIG. 10 is a view, corresponding to FIG. 9, of a modified form of the apparatus of FIGS. 7 and 8.

The apparatus to be described is particularly arranged so as to be suitable for examining sheet material in the form of tin plate strip 10 being produced by a tin plate mill. Tin plate is widely used in the canning industry and any faults in the tin plate and in particular any holes through the tin plate must be detected and rejected since they will allow dangerous deterioration of the contents of any can made from that tin plate. It is therefore desired to produce an apparatus which will detect holes as small as pin holes (down to approximately 25 $\mu m \times 25$ $\mu m$) in tin plate strip which is approximately 1 meter wide and is moving past the detecting apparatus at 600 m/min. A powerful beam of radiation is scanned across the tin plate as it is passing from the strip mill and the radiation passing through any pin holes in the tin plate is detected. Clearly, this requires, in the example given, a rapid scanning apparatus and also apparatus suitable for detecting small amounts of radiation.

The pin holes may be rough or smooth and may be at right angles or at other angles to the tin plate surface and so it is difficult to generalise about the form of radiation passing through the pin holes. Some pin holes will contain bright flow melted tin, thereby causing minimal attenuation of transmitted radiation even if multiple internal reflections occur. Other pin holes will be internally ragged or dull resulting in strong attenuation of all internally reflected light. Other problems to be overcome relate to the fact that it is not desired to restrain the tin plate strip and so some flutter will occur, the plane of the tin plate sometimes flapping up and down to the extent of several centimeters.

The apparatus illustrated in FIGS. 1 and 2 comprises a radiation source in the form of a 5 mW HeNe laser 11 which is useful in the present instance because this type of laser has an output power which is below the limit where stringent safety precautions need to be taken, it is relatively cheap to replace, and, in the commercially available version, the laser head has pre-aligned machined grooves allowing quick and simple replacement without the need for adjustment. The beam of radiation from the laser 11 is passed to an attenuator in the form of an acousto-optic modulator 12. An example of the type of acousto-optic modulator which may be used is the model 305 Acousto-Optic Modulator made by Coherent Associates.

The modulator comprises a Bragg glass cell which is strained by a bonded transducer array. The apparatus has a 120 nanosecond rise and fall time, and a 10,000:1 extinction ratio. When the glass cell is strained light is diffracted so as to be absorbed around an aperture (or passed through the aperture) and when the glass cell is not strained the beam passes through the aperture (or is absorbed around the aperture).

The modulator 12 is followed by beam shaping lenses 13 the function of which will be described later.

The beam passes from the beam shaping lenses 13 to a multifaceted mirror drum 14. The mirror drum has 12 mirror facets to provide a 40° total scan angle and is driven by a 24000 rpm motor 20. The mirror drum 14 is arranged so that alternate facets are at a slightly different angle with respect to the axis of rotation. Thus, referring to FIG. 2 the beam will be scanned along a path A by a first facet of the mirror drum, the next facet will scan the beam along a path B, the next facet will scan the beam along a path A and so on. The two beams A and B are reflected upwardly from the mirror drum 14 through two cylindrical lenses 25 (one for each path A, B) to two plane mirrors 17A and 17B, (one for the beam path A and B). The beam paths A and B are reflected downwardly respectively to mirrors 53, 54 and thence to the sheet material 10. It will be seen from FIG. 2 that the parts of the beam paths A and B directed at the sheet material are tilted respectively downstream and upstream with respect to a perpendicular from the sheet material. As mentioned before, if the sheet material is rolled and there are holes therethrough the holes generally thereafter tilt in an upstream or downstream direction and by tilting the beams produced by successive facets of the mirror drum in this way these tilted holes can be more readily detected without affecting the detection of normal holes.

The facets of the mirror drum and the sheet material are conjugate with respect to the lenses 25. The lenses 25 in combination with the beam shaping lenses 13 convert the circular cross-section of the laser beam to a slit-shaped cross-section at the tin plate 10 to be examined. The scanned beam path from the lenses 25 is passed to plane mirrors 17A, 17B which effectively fold the optical paths A and B so as to reduce the height of the instrument. The tin plate strip 10 moves in the direction of the arrow in FIG. 2.

The apparatus thus far described includes a container so as to reduce the amount of ambient light passing to the surface of the tin plate and this container 19 may incorporate flexible baffles which allow the tin plate to flap without damaging the apparatus.

The light collecting optical apparatus is provided below the tin plate strip 10. It comprises six perspex light guides 22 generally in the form of rectangular cross-section strips, a first end face 23 (FIG. 3) of each being placed immediately below the scan line of the beam of radiation and being rectangular in shape, so that the two longer sides 26, 27 (200 mm long) thereof are parallel to the line of scan and the two shorter sides 28, 29 (20 mm long) are at right angles thereto.

The second end face 24 at the opposite end of each strip 22 is provided which, like the first end face 23, is rectangular and, as is illustrated in FIG. 4, has two longer sides 31, 32 (120 mm) and two shorter sides 33, 34 (20 mm).

The light guides 22 each have a rectangular cross-section throughout their lengths and sides 26, 27 correspond with sides 31, 32. The light guides each gradually change size between the two opposite end faces 23, 24.

As is clear from FIGS. 1 and 2, the first end faces 23 are each arranged so that their sides 26 are colinear as are their sides 27. Also the first end faces 23 of each light guide 22 are coplanar. The sides 28, 29 of each light guide abut one another so that they are end to end. In this way the light guides 22 provide an elongate light collecting area approximately 1.2 m in length and 20 mm wide.

Furthermore, the light guides are shaped so that their opposite ends, provided by the second end faces 24 are arranged side by side so that although the second end faces 24 of each light guide are coplanar, the sides 28 of each light guide are colinear as are the sides 29 and the sides 26, 27 of adjacent light guides abut one another.

The effect of this is to provide a light transmitting set of second end faces which are compact rather than elongate and are generally of overall dimensions 120 mm × 120 mm which can be readily matched to a photomultiplier.

The first end faces 24 of the light guides are arranged to one side which is preferable from the point of view of servicing and maintenance. It is necessary not only to arrange the light guides 22 to pass through 90° but also to be twisted as is clear from FIGS. 1 and 2. That is, the guides 22 are twisted about their own longitudinal axes as well as the axis itself being curved through 90°.

The second end faces are arranged so as to be immediately adjacent a photomultiplier 36 although a red transmitting gelatine filter and/or polarising filter 37 may be provided between the second end faces and the photomultiplier 36. The photomultiplier 36 has an S20 photocathode of 190 mm diameter.

The collection optical apparatus will be enclosed as far as possible to exclude ambient light although this is less important since the light guides 22, being of perspex of refractive index with respect to air of 1.5, are arranged to internally reflect light reflected from pin holes through the tin plate strip.

In order to facilitate threading of the tin plate through the apparatus the top half of the apparatus may be hinged so that it can be swung upwards from the line during threading.

The signal produced by the photomultiplier 36 is passed to a signal processing apparatus which is illustrated in diagrammatic form in FIG. 5. The photomultiplier 36 is driven by an EHT supply 38 and the signal from the photomultiplier 36 is passed to a pre-amplifier 39 where the amplified signal is divided, part being passed to a filter module 40. The filter module 40 contains a band pass filter tuned to pass only frequencies associated with the laser spot scanning over small pin holes which will be to a close approximation the fundamental frequency of the laser spot scanning over a sharp edge since the small pin holes will be several times smaller than the laser spot. Thus if the laser spot size x scanning speed can be kept constant across the scan a very narrow band pass filter can be employed. By the use of this filter module the signal to noise ratio of the final threshhold signal may be improved by two to three times compared with the raw photomultiplier signal. The other signal from the pre-amplifier 39 is passed to a margin module 41 which produces a signal to switch the acousto-optical modulator 12 which will in turn reduce the laser beam intensity when scanning across large pin holes or beyond the edges of the strip. This is required to prevent possible damage to the photomultiplier 36 and to reduce the dark current noise which would be induced by a very high light level falling on to the cathode of the photomultiplier thereby reducing the sensitivity of the instrument. Thus the margin module 41 detects a sudden increase in the level of signal produced by the photomultiplier as the beam is scanned across a large hole or beyond the margin switches on the acousto-optical modulator 12 so that, as above described with respect to the modulator, the output is reduced by a factor of approximately 100.

The signal from the filter module 40 is passed to a self adjusting sensitivity module 42 which also receives an output from the margin module 41 and threshholds the signal to output reject logic pulses. The threshhold level will be derived from a circuit which will measure the noise level during the scan over the tin plate and automatically set the threshhold level so that maximum sensitivity is always employed despite signal changes due to ageing of the laser and the photomultiplier or changes in ambient light level. The threshhold level will depend upon the average time period deemed desirable between spurious rejection pulses since the noise pulse height time relation will be approximately a gaussian distribution and therefore there will exist a statistical chance of a noise pulse exceeding the threshhold level whatever it might be. This period could be set so that, on average, one spurious rejection per day occurred.

The reject logic signal could, of course, be used in the same manner as that from the present pin hole detector to reject as waste any cut sheet containing a pin hole. Thus the output signal from the module 42 may be fed to a control unit 43 which controls a sorting apparatus to move a sheet containing a pin hole on to a separate stack. This apparatus may incorporate delay means operated in accordance with the speed of movement of the sheet material.

The apparatus thus far described may be used as follows. During the initial threading of the tin plate strip through the apparatus the components above the line of the tin plate may be pivoted away from the tin plate line and then pivoted back to the positions shown in FIGS. 1 and 2. The laser 11 produces a beam 15 which is passed by the acousto-optic modulator 12 through the beam shaping lenses 13 to the scanner mirror drum 14. As has already been described the beam 15 is passed either along path A of path B depending upon which facet of the mirror drum 14 it strikes. Alternate facets pass the beam along path A or B. It will be understood from FIG. 2 that paths A and B are tilted with respect to the perpendicular from the sheet material, the path B being tilted in an upstream direction and the path A in a downstream direction.

Thus successive scans will be directed at the sheet material from upstream or downstream with respect to the direction of motion of the sheet material.

The various factors such as the speed of rotation of the mirror drum, the width of the beam when focused on the sheet material, are arranged so that successive beams along path A overlap and successive beams along path B overlap so that the entire sheet material is scanned twice, once by a beam from along the path A and once by a beam from along path B.

In this way a rectangular section beam is swept across the tin plate from side to side at right angles to the direction of movement of the tin plate and the speed is arranged such that successive scans are spaced by a distance less than the width of the beam whereby all of the tin plate is scanned by the laser beam. Any light passing through a pin hole in the tin plate whether tilted or not will produce a light signal below the tin plate which may be scattered but which will be at such an angle as to be able to pass through the first end face of one of the light guides 22. Once the light has passed into the light guide 22 it is internally reflected by the light guide 22 so as to be passed from the first end face to the second end face at the opposite end of the light guide where the light passes through the filter or filters 37 to be detected by the photomultiplier 36. The photomultiplier will record this light. The position across the scan, and hence the position of the pin hole across the width of the sheet, may be determined from a synchronization mechanism synchronized with rotation of the mirror drum which will be able to indicate the position of the scanned beam when the pin hole is detected.

The photomultiplier produces a signal of the form shown in FIG. 7 in which 46 indicates the saturated signal at the end of a scan beyond the end of the tin plate and 47 a pulse produced by a pin hole. The signal which is processed in the manner described with reference to FIG. 3 and an output is produced which may be utilised to reject sheets of tin plate in which a pin hole is present, or simply record the signal.

It will be understood that the light guides, therefore, collect any light signal produced within an area which is approximately 1200 mm long and 20 mm wide and pass this to an area which is 120 mm long and 120 mm wide which may be readily mounted immediately adjacent a commercially available photomultiplier. The advantage of such a system is that only a single photomultiplier is required whereby a saving in cost is effected and also any discrepancies between different photomultipliers are eliminated.

Samples of tin plate have been examined and it has been found that the pin holes are not always arranged so that their axes are normal to the surface of the tin plate. (We use "axes" in a loose sense since clearly most pin holes will not be of geometrical shape). In many cases, the axes of the pin holes lean forwards or backwards relative to the direction of movement of the tin plate. It would seem that this arises owing to the rolling of the tin plate in which as the tin plate is stretched by the rollers the axis of the pin hole is moved away from a direction generally transverse to the plane of the tin plate.

Because successive scans, which overlap, are tilted with respect to the direction of movement of the tin plate, any pin holes which lean forwards or backwards as described above will be recorded by the apparatus. Furthermore pin holes which are at right angles to the strip will also be recorded as there will be sufficient scatter from the two beams to produce a sufficient signal.

It will be observed that for the most part, the laser beam strikes the upper surface of the tin plate sample and is then reflected therefrom, since the tin plate has a reflective or semi-reflective surface. A retro-reflective surface is provided to intercept this beam A or B, the retro-reflective surface being in the form of a strip of tape 61 which extends from side to side as illustrated in FIG. 7 so as to intercept the beam A or B throughout the length of its scan and the retro-reflective tape 61 reflects the beam A or B in a slightly diffuse manner back along its path (as illustrated in FIGS. 7 and 8) so that the diffuse beam 60 thereby passes back to the tin plate strip, is reflected from the upper surface thereof via mirrors 53 or 54 to the mirror 17A or 17B and thence back through the optical arrangement to the lens 25. However the lens 25 is sufficiently narrow as to only intercept part of the beam passing whence the diffuse beam can be passed to a photomultiplier.

It will be understood, therefore, that the photomultiplier will provide an output signal depending on the reflectivity of the upper surface of the tin plate strip and the tin plate strip being examined respectively by a highly defined area formed by the incident laser beam and an ill defined larger area formed by the beam reflected from the retro-reflective tape.

Such a surface inspection technique has a number of advantages. It is extremely tolerant to tilt of the tin plate surface where at least ±5° of tilt in any plane, as is illustrated in chain lines in FIG. 8, and vertical displacement of the strip by several cm can be accommodated.

Furthermore, its sensitivity to large absorbing defects (greater than 5 mm wide) will be increased over the sensitivity obtained with alternative systems. An increase in signal value will be produced. The sensitivity of the retro-reflective system to surface dent defects (eg scrape marks) is enhanced compared with other simple scanning systems because of the manner in which local surface tilts can be detected in the presence of overall tilts of the strip. The signal processing electronics required to process the signal produced by the photomultiplier is well known.

There is, however, one difficulty with the use of the surface inspection apparatus as is illustrated in FIG. 9 which shows an enlarged end view of the part of the apparatus adjacent a margin of the tin plate strip 10. As the beam 15 approaches the margin of the tin plate strip 10 then the retro-reflected diffuse beam 60 will reach the margin 64 before the well defined beam 15 and at this point the acousto-optic modulator 12 will be switched off so that a marginal area of the strip 10 will not be examined by the highly defined laser beam 15. This difficulty can be overcome, however, as follows with reference to FIG. 10 which shows a view similar to FIG. 9.

In the apparatus a half-wave plate 71 is incorporated below the retro-reflector 61 and a polarising filter 73 is mounted above the first end faces 23 of the light guides 22 and below the tin plate 10. The effect of these components is illustrated in FIG. 11. The laser beam 15 incident on the tin plate sample is naturally polarised and the plane of polarisation is indicated by the arrow 74. The beam reflected from the tin plate 10 passes through the half-wave plate 71 and its plane of polarisation is rotated by 45° indicated by arrow 75; it is reflected by the retro-reflective tape 61 and passes through the half-wave plate 71 again which rotates the plane of polarisation by a further 45° indicated by arrow 76. This reflected beam 60 will then be cut out by the polarising filter 73 whose orientation is such as to allow the incident beam 15 to pass therethrough but will cut out the beam 60 which is polarised at 90° thereto. In this way, therefore, any light from the retro-reflector passing beyond the edge of the margin before the main incident beam reaches the edge of the margin will be cut out by the polarising filter 73.

Although the apparatus has been described for use with measuring pin holes in a tin plate sample, it is not restricted to use with tin plate. It may equally be used with other materials such as paper and, without the surface inspection option, may be utilised for non reflective materials. Although the preferred apparatus has been described as suitable for detecting pin holes in sheet material, that is, holes below, say $100 \mu m \times 100 \mu m$, it may also be used to detect larger holes. In practice these would be detected in much the same way except that the full power of the laser beam will pass through to the radiation detector and they will be treated as if they were an edge margin of the sheet. The signal processing apparatus described will therefore produce an output indicating that the large size holes are margins of the sheet material and it is then required that the signal processing apparatus include a further component to determine that the signal is not in fact due to the margin of the sheet but due to a large hole. This may be done by a number of means, for example, a counting or timing device which may predict when the beam will reach the edge margin of the sheet material and will indicate that any signal apparently from the margin of the sheet material which appears at other times will in fact be produced by a large hole.

In the described apparatus, as the beam passes the edge margin of the strip it is attenuated by the acousto-optic modulator 12. Alternatively, the signal used to detect the edge margin of the strip may be utilised to reduce the voltage applied to the laser and thereby reduce the intensity of the laser beam. In this case an acousto-optical modulator 12 might not be required.

The preferred embodiments of the apparatus described are capable of consistently measuring pin holes $25 \mu m \times 25 \mu m$ is sheet material moving at up to 600 m/min. Under good conditions, however, the apparatus may indicate pin holes down to $7\frac{1}{2} \mu m \times 7\frac{1}{2} \mu m$ and with a more powerful laser this lower limit could be improved even further. Another way of improving the minimum size of pin holes to be detected would be to utilise an ultra-violet source of radiation when it is easier to improve the signal to noise ratio by reducing the amount of background radiation but this raises difficulties in production line use of operator safety.

The invention is not restricted to the details of the foregoing example.

What we claim is:

1. Apparatus for detecting holes through opaque or generally opaque sheet material moving in a first direction comprising a radiation source, means for directing a beam of radiation from the source at the sheet material and for scanning the beam thereacross in a direction transverse to said first direction, characterised in that said beam directing means is arranged so that the beam, in use is directed at said sheet material along a path tilted from the perpendicular to the sheet material in an upstream direction with respect to the direction of movement of the sheet material during some scans and in a downstream direction during other scans, means located so as to be on the opposite side of the sheet material to the incident radiation to collect radiation passing through holes in the sheet material, said collection means comprising at least one radiation guide comprising transparent material having a high refractive index relative to its surroundings, a first face of the radiation guide being shaped and positioned to collect the radiation passing through holes in the sheet material, a second face of the radiation guide opposite the first face being shaped to pass the radiation collected by the first face to a radiation detector, and the faces joining the first and second faces being arranged such as to internally reflect radiation from said first face to said second face.

2. Apparatus as claimed in claim 1 in which the first face of the radiation guide is planar and rectangular, one pair of sides of the rectangle being parallel to the direction of scanning.

3. Apparatus as claimed in claim 2 in which said one pair of sides is longer than the other pair of sides.

4. Apparatus as claimed in claim 3 in which the second face is planar and generally rectangular, the radiation guide being of rectangular section between the first and second faces each of the pair of sides of the rectangular section of the second face which corresponds to said one pair of sides being smaller than each of said one pair of sides.

5. Apparatus as claimed in any of claims 1 to 4 in which there are provided a plurality of radiation guides, each having generally similar shaped rectangular first faces, the radiation guides being arranged end to end so that their said one pair of sides are colinear and their first faces are coplanar.

6. Apparatus as claimed in claim 5 in which the second faces of said radiation guides are each generally similar, and the second faces are coplanar and arranged side by side.

7. Apparatus as claimed in claim 1 in which the or each radiation guide is of a material having a refractive index with respect to air of approximately 1.5.

8. Apparatus as claimed in claim 1 in which the or each radiation guide is of perspex.

9. Apparatus as claimed in claim 1 in which means are provided to reduce the ambient light falling on the radiation collector.

10. Apparatus as claimed in claim 1 in which the radiation source comprises a laser.

11. Apparatus as claimed in claim 1 in which the scanning means comprises a multi-faceted mirror drum.

12. Apparatus as claimed in claim 1 in which retro-reflective means is provided to reflect back to the sheet material radiation which has been reflected by the sheet material.

13. Apparatus as claimed in claim 12 in which means is provided for preventing radiation reflected by the retro-reflective means and passing past the edge of the sheet material as the beam passes beyond the edge of the sheet material from reaching the radiation detector.

14. Apparatus as claimed in claim 13 in which the prevention means comprises means for polarising the beam of radiation directed at the sheet material, means for rotating the plane of polarisation of the radiation reflected from the surface of the sheet material by 45° means for rotating the plane of polarisation of radiation reflected by the retro reflective means by 45°, and polarised filter means provided in front of the radiation collecting means, whereby radiation reflected by the sheet material, and the retro-reflective means will not pass through the polarising filter.

15. Apparatus as claimed in claim 13 in which the overload prevention means comprises an acousto-optical device provided in the beam path and signal processing means for detecting an excess signal produced by the radiation detector connected to switch the acousto-optical device to attenuate the beam.

16. Apparatus as claimed in claim 1 including a radiation detector in which means is provided for preventing the overloading of the radiation detector as the beam is scanned beyond the edge of the sheet material.

17. Apparatus as claimed in claim 16 in which the overload prevention means comprise control means for detecting an excess signal in the radiation detector.

18. Apparatus as claimed in claim 1 including a radiation detector connected to pass a signal to a signal processing apparatus, the signal processing apparatus including a band pass filter arranged to pass a signal corresponding to a small hole in the sheet material.

19. Apparatus as claimed in claim 1 in which some facets of the mirror drum are at different angles to the axis of rotation of the drum with respect to some other facets.

20. A method for detecting holes through an opaque or generally opaque sheet material moving in a first direction comprising directing a beam of radiation at the sheet material and scanning the beam thereacross, characterised by directing the beam at said sheet material along a path tilted from the perpendicular to the sheet material in an upstream direction with respect to the direction of movement of the sheet material during some scans and in a downstream direction during other scans, collecting radiation passing through holes in the sheet material by means of a radiation guide, the guide internally reflecting radiation received by a first face thereof so as to pass the radiation to a second face thereof, detecting radiation received at the second face and producing an output signal in accordance with the radiation detected.

21. A method as claimed in claim 20 in which the radiation is collected from an elongate area parallel with the line of scan, and is passed to a compact area adjacent the radiation detector whereby a single radiation detector is utilised.

22. A method as claimed in claims 20 or 21 in which the beam of radiation is scanned across the sheet material in such a manner as to cover all of the sheet material.

23. A method as claimed in claim 22 in which the sheet material is moved at a rate of approximately 600 m/min.

24. A method as claimed in claim 20 in which the sheet material to be inspected reflects at least a portion of the radiation incident on it and in which the beam reflected from the sheet material is retro-reflected back to the sheet material so as to be reflected a second time by the sheet material before collection.

25. A method as claimed in claim 24 in which radiation which has been retro-reflected and has passed beyond the edge of the sheet material as the beam passes beyond the edge of the sheet material is prevented from reaching the radiation detector.

26. A method as claimed in claim 25 in which the beam of radiation incident on the sheet material is polarised, the plane of polarisation of the beam reflected by the material is rotated by 45° before reaching the retro-reflector, and the retro-reflected beam is polarised by a further 45°, and a polarised filter means situated before the radiation guide means is aligned so as to absorb the retro-reflected beam.

27. A method as claimed in claim 20 in which overloading of the radiation detector is prevented as the beam is scanned beyond the edge of the sheet material.

28. A method as claimed in claim 27 in which overloading of the radiation detector is prevented by detecting an increase in the signal produced by the radiation detector and attenuating the incident beam in accordance therewith.

29. A method as claimed in claim 27 in which overloading of the radiation detector is prevented by detecting an increase in the signal produced by the radiation detector and reducing the sensitivity of the radiation detector.

30. A method as claimed in claims 20, 21, 24, 25, 26, 27, 28 or 29 for detecting holes of dimensions less than 100 $\mu m \times 100$ $\mu m$.

31. A method as claimed in claim 30 for detecting holes of dimensions of the order of 25 $\mu m \times 25$ $\mu m$.

* * * * *